(12) United States Patent
Sugioka et al.

(10) Patent No.: US 10,814,202 B2
(45) Date of Patent: Oct. 27, 2020

(54) INFORMATION PROCESSING DEVICE, SENSOR DEVICE, AND INFORMATION PROCESSING SYSTEM

(71) Applicant: SONY CORPORATION, Tokyo (JP)

(72) Inventors: Motoyuki Sugioka, Tokyo (JP); Hirokazu Hashimoto, Kanagawa (JP); Sho Murakoshi, Tokyo (JP); Kazuhiro Nakagomi, Tokyo (JP); Yoshiyuki Miyamoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/306,074

(22) PCT Filed: May 16, 2017

(86) PCT No.: PCT/JP2017/018302
§ 371 (c)(1),
(2) Date: Nov. 30, 2018

(87) PCT Pub. No.: WO2018/008259
PCT Pub. Date: Jan. 11, 2018

(65) Prior Publication Data
US 2019/0134482 A1  May 9, 2019

(30) Foreign Application Priority Data

Jul. 5, 2016 (JP) .................................. 2016-133403

(51) Int. Cl.
*A63B 69/36* (2006.01)
*A63B 69/38* (2006.01)
(Continued)

(52) U.S. Cl.
CPC .......... *A63B 69/3608* (2013.01); *A63B 69/00* (2013.01); *A63B 69/36* (2013.01);
(Continued)

(58) Field of Classification Search
CPC ..... A63B 69/3608; A63B 69/00; A63B 69/38; A63B 69/36; G06K 9/0055; G06K 9/00342; G06T 7/248; G09B 19/0038
See application file for complete search history.

(56) References Cited

U.S. PATENT DOCUMENTS 8,766,977 B2 * 7/2014 Kim ..................... G06T 7/20
345/420
2014/0079290 A1 3/2014 Nakano et al.

FOREIGN PATENT DOCUMENTS

CN 103685862 A 3/2014
CN 106573168 A 4/2017
(Continued)

OTHER PUBLICATIONS

International Search Report and Written Opinion of PCT Application No. PCT/JP2017/018302, dated Aug. 1, 2017, 02 pages of translation and 11 pages of ISRWO.

*Primary Examiner* — Jeffrey S Vanderveen
(74) *Attorney, Agent, or Firm* — Chip Law Group

(57) ABSTRACT

An information processing device includes a motion information acquiring section that acquires a plurality of pieces of motion information showing a series of motions of a same kind performed by a plurality of users and a reference timing extracting section that extracts a reference timing based on a plurality of pieces of the motion information. Also included are an image information acquiring section that acquires a plurality of series of image information corresponding to a plurality of pieces of the motion information and a synchronization processing section that synchronizes a plurality of pieces of the image information based on the reference timing.

14 Claims, 14 Drawing Sheets

(51) Int. Cl.
    *A63B 69/00*     (2006.01)
    *G06T 7/246*     (2017.01)
    *G06K 9/00*     (2006.01)
    *G09B 19/00*     (2006.01)

(52) U.S. Cl.
    CPC ............ *A63B 69/38* (2013.01); *G06K 9/0055* (2013.01); *G06K 9/00342* (2013.01); *G06T 7/248* (2017.01); *G09B 19/0038* (2013.01)

(56) References Cited

FOREIGN PATENT DOCUMENTS

| | | | | |
|---|---|---|---|---|
| EP | 3181203 A1 | 6/2017 | | |
| JP | 2004-260765 A | 9/2004 | | |
| JP | 2004260765 A | * 9/2004 | ............... | H04N 5/93 |
| JP | 2006-230630 A | 9/2006 | | |
| JP | 2009-106323 A | 5/2009 | | |
| JP | 2014-064109 A | 4/2014 | | |
| JP | 2014-064110 A | 4/2014 | | |
| JP | 201464109 A | * 4/2014 | ............... | H04N 5/93 |
| JP | 2014-187481 A | 10/2014 | | |
| JP | 2015-061237 A | 3/2015 | | |
| JP | 201561237 A | * 3/2015 | ............. | H04N 5/262 |
| KR | 10-0620873 B1 | 8/2006 | | |
| KR | 10-2014-0043665 A | 4/2014 | | |
| KR | 10-2017-0043560 A | 4/2017 | | |
| WO | 2006/135160 A1 | 12/2006 | | |
| WO | 2016/024392 A1 | 2/2016 | | |
| WO | WO-2016024392 A1 | * 2/2016 | ............. | A63B 69/36 |

\* cited by examiner

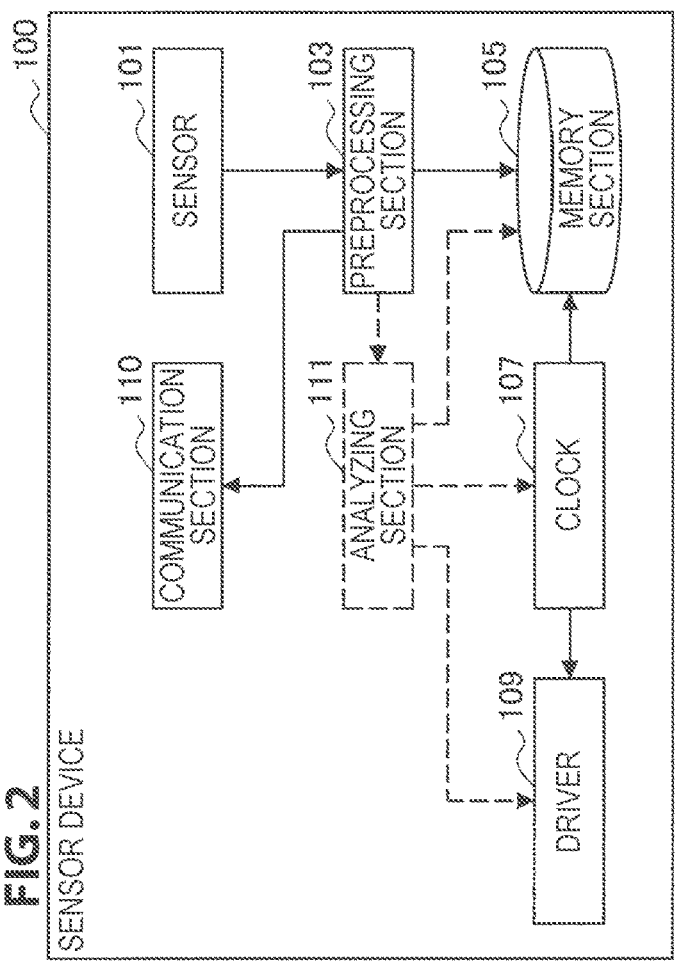
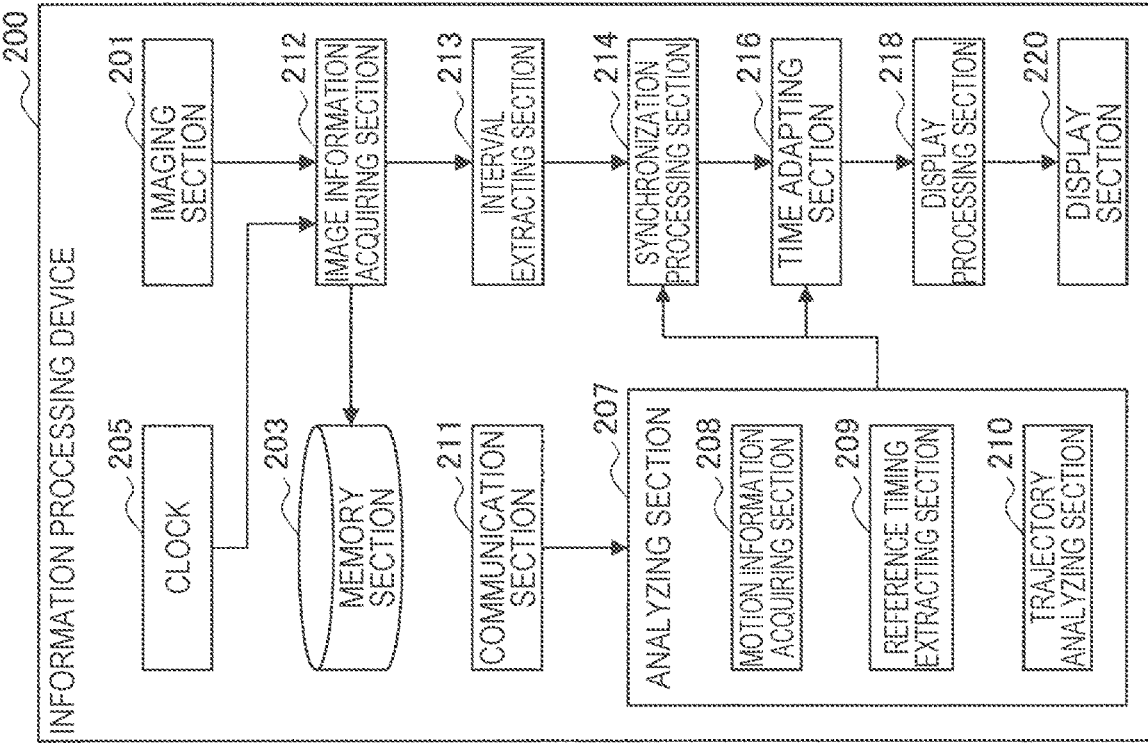
FIG. 2

INFORMATION PROCESSING DEVICE, SENSOR DEVICE, AND INFORMATION PROCESSING SYSTEM

CROSS REFERENCE TO RELATED APPLICATIONS

This application is a U.S. National Phase of International Patent Application No. PCT/JP2017/018302 filed on May 16, 2017, which claims priority benefit of Japanese Patent Application No. JP 2016-133403 filed in the Japan Patent Office on Jul. 5, 2016. Each of the above-referenced applications is hereby incorporated herein by reference in its entirety.

TECHNICAL FIELD

The present disclosure relates to an information processing device, a sensor device, and an information processing system.

BACKGROUND ART

Hitherto, for example, in Patent Literature 1 described in the below, described is a technique which has supposed extracting a scene corresponding to a play state of a sport by a user with higher accuracy.

CITATION LIST

Patent Literature

Patent Literature 1: JP 2014-187481A

DISCLOSURE OF INVENTION

Technical Problem

For example, in sports in which a swing is performed by a series of motions, such as baseball, tennis, and golf, there is a request to want to grasp points to be improved in a user's own swing by arranging the moving image of a swing becoming a good example and the moving image of a photographed user's own swing alongside and by reproducing and displaying them.

However, the speed of a swing is greatly different depending on users, and a start timing of a swing and an end timing of the swing are also greatly different depending on the users. For this reason, even if merely arranging the respective moving images of swings alongside and reproducing them, it is difficult to compare the both moving images concretely, and it is substantially difficult to find out the above mentioned points to be improved by the comparison.

Then, in the case where a plurality of series of images are arranged alongside and displayed, it has been desired to make the both images easy to be compared.

Solution to Problem

According to the present disclosure, there is provided an information processing device including: a motion information acquiring section that acquires a plurality of pieces of motion information showing a series of motions of a same kind; a reference timing extracting section that extracts a reference timing on the basis of a plurality of pieces of the motion information; an image information acquiring section that acquires a plurality of series of image information corresponding to a plurality of pieces of the motion information; and a synchronization processing section that synchronizes a plurality of pieces of the image information on the basis of the reference timing.

In addition, according to the present disclosure, there is provided a sensor device including: a sensor that detects a plurality of pieces of motion information showing a series of motions of a same kind; and a transmitting section that transmits the motion information to an information processing device to make an information processing device perform processing for extracting a reference timing on the basis of a plurality of pieces of the motion information, processing for acquiring a plurality of series of image information corresponding to a plurality of pieces of the motion information, and processing for synchronizing a plurality of pieces of the image information on the basis of the reference timing.

In addition, according to the present disclosure, there is provided an information processing system including: a sensor device that detects a plurality of pieces of motion information showing a series of motions of a same kind; and an information processing device that includes a motion information acquiring section that acquires the motion information from the sensor device, a reference timing extracting section that extracts a reference timing on the basis of a plurality of pieces of the motion information, an image information acquiring section that acquires a plurality of series of image information corresponding to a plurality of pieces of the motion information, and a synchronization processing section that synchronizes a plurality of pieces of the image information on the basis of the reference timing.

Advantageous Effects of Invention

As described in the above, according to the present disclosure, in the case where a plurality of series of images are arranged alongside and displayed, it becomes possible to make the both images easy to be compared.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 2 is a block diagram showing a schematic functional constitution of a sensor device and an information processing device according to one embodiment of the present disclosure.

MODE(S) FOR CARRYING OUT THE INVENTION

Figure 1:
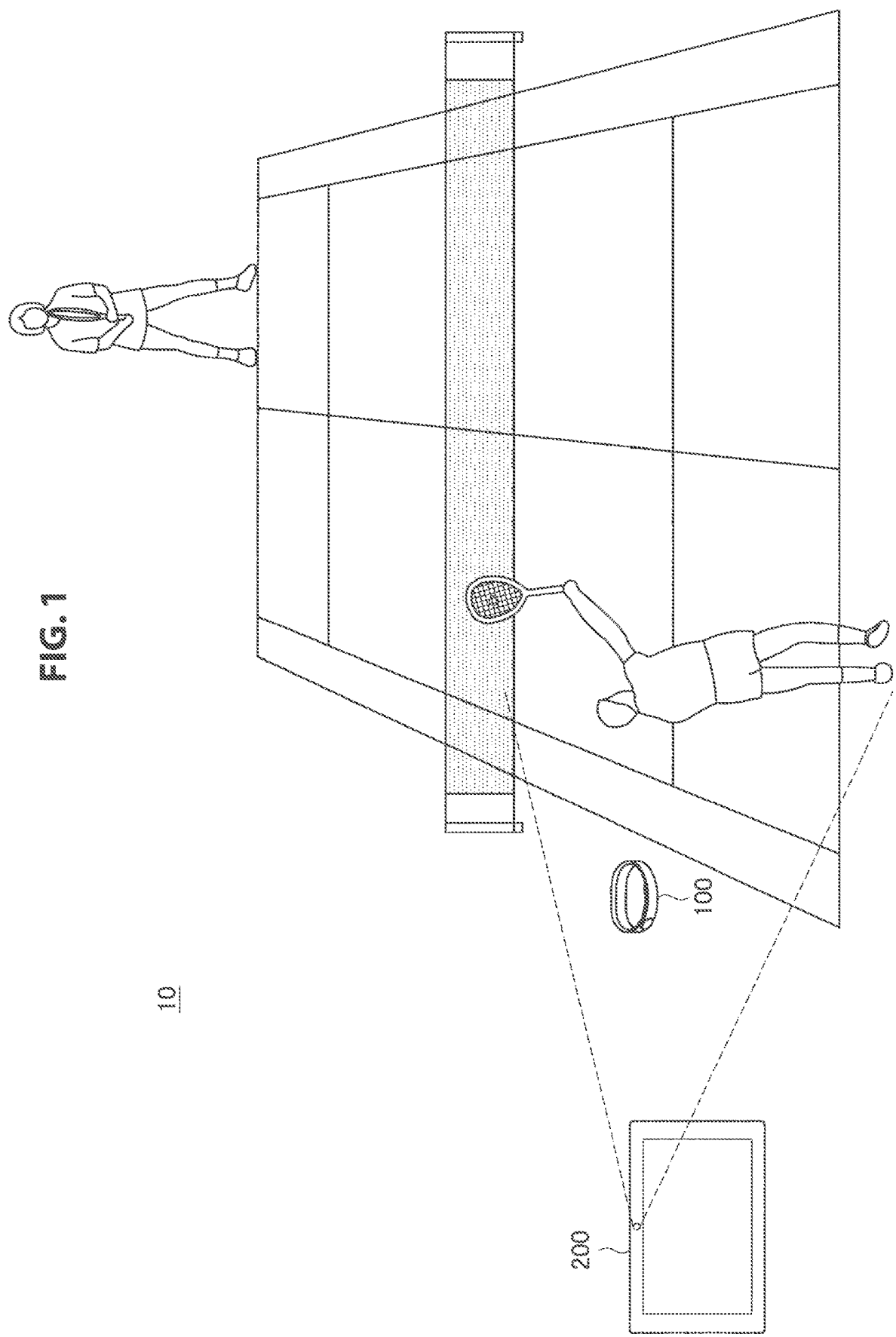
FIG. 1 is an illustration showing an outline of an information processing system according to one embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

It should be noted that description is given in the following order.
1. Constitution example of system
2. Device constitution
3. Processing performed by information processing device
4. Example of having combined motion recognition and image processing

1. Constitution Example of System

First, with reference to FIG. 1, a constitution of an information processing system according to the first embodiment of the present disclosure is described. FIG. 1 is an illustration showing an outline of the information processing system according to one embodiment of the present disclosure. Referring to FIG. 1, an information processing system 10 includes a sensor device 100 and an information processing device 200.

The sensor device 100 is attached to a user who is playing sports, or to sport tools used by the user. In the example shown in FIG. 1, a situation where a user is playing tennis in a tennis court, is shown. In the case of attaching the sensor device 100 to the user, for example, as shown in the illustration, the sensor device 100 may be shaped in a form of a bracelet, and may be attached directly to the body of the user. Moreover, in the case of attaching the sensor device 100 to a sport tool (for example, in the case of tennis, a racket, wear, shoes, a wristband, etc., and in the case of golf, a golf club), the sensor device 100 may be wound around a shaft portion etc., may be sewn or pasted on a cloth, or may be built in tools beforehand.

Here, the sensor device 100 acquires sensor information showing the behavior of the user who is playing a sport. The behavior of the user shown by the sensor information may be, for example, physical movements (position, speed, acceleration, etc.) of the user or the tool. In order to acquire such sensor information, for example, the sensor device 100 includes at least one sensor. The sensor detects, for example, acceleration, angular velocity, vibration, temperature, time, a position (for example, a position on the ground surface expressed by latitude and longitude, or a relative position to a court etc.) or the like. The sensor device 100, for example, accumulates the sensor information acquired by doing in this way. The accumulated sensor information, for example, may be transmitted to the information processing device 200 when the user has connected the sensor device 100 and the information processing device 200 after having ended the play.

The information processing device 200 includes a camera, and captures a play image of a sport. The information processing devices 100 is a mobile device, for example, such as a smart phone and a tablet terminal. The play image may be a moving image on at least a part of which the user who is playing a sport is reflected. The information processing device 200, for example, is installed in the surrounding of the tennis court where the user is playing a sport, and captures a play image. The data of the captured play image are at least temporarily accumulated in the information processing device 200. The information processing device 200 may receive the sensor information acquired by the sensor device 100 during photographing of the play image.

On the basis of the sensor information received here, the information processing device 200 performs processing for extracting a play image in the sport which the user is playing, only for a predetermined period. The extracting of the play image by the information processing device 200 is described in detail later.

In this connection, the information processing device 200, for example, may upload the play image to which a digest image and additional information have been set, to a server being not illustrated. Alternatively, the information processing device 200 may upload the captured play image to the server, the sensor device 100 may also upload sensor information to the server, and then, various kinds of processing described in the below may be performed in the server

2. Device Constitution

Next, with reference to FIG. 2, a functional constitution of each of devices included in the information processing system according to one embodiment of the present disclosure is described. FIG. 2 is a block diagram showing a schematic functional constitution of a sensor device and an information processing device according to one embodiment of the present disclosure. Hereinafter, the functional constitution of each of the devices is described with reference to FIG. 2. In this connection, the hardware constitution for realizing these functions is mentioned later.

(Sensor Device)

The sensor device 100 includes a sensor 101, a preprocessing section 103, a memory section 105, a clock 107, a driver 109, and a communication section 110. The sensor device 100 may further include an analyzing section 111. In the case where the sensor device 100 includes the analyzing section 111, the analyzing section 111 performs processing similar to that in an analyzing section 204 of the information processing device 200, and transmits an analysis result to the information processing device 200 via the communication section 110. Moreover, in the case where the sensor device 100 includes the analyzing section 111, image information may be acquired by the sensor device 100 side, and the same processing with that in the information processing device 200 may be performed by the sensor device 100 side.

The sensor 101 detects, for example, acceleration, angular velocity, vibration, temperature, time, a position or the like. In more concrete terms, the sensor 101 may include, for example, an acceleration sensor, an angular velocity sensor (gyro sensor), a vibration sensor, a temperature sensor, a pressure sensor (including a depression switch), or a GPS (Global Positioning System) receiver. In this connection, the sensor device 200 may be provided integrally with the information processing device 200. Moreover, the sensor device 200 may acquire the motion information of the user with motion capture or the like.

The preprocessing section 103 executes preprocessing of data detected by the sensor 101. The preprocessing may be, for example, amplification of the detected data, filtering of the data equal to or less than a threshold, and so on. In this connection, depending on the kind of the sensor 101, the data may be supplied to the memory section 105 not necessarily via the preprocessing section 103.

The memory section 105 stores temporarily the data that have been detected by the sensor 101 and have been processed by the preprocessing section 103 as required, as the sensor information. At this time, the sensor information is stored with a time stamp given by the clock 107.

Here, the sensor information stored in the memory section 105 is transmitted to the information processing device 200 through the communication section 110. The sensor information may be transmitted from the sensor device 100 to the information processing device 200 in real time when having been generated, or may be transmitted afterwards.

The clock 107 regulates the time used in the sensor device 100. The clock 107 regulates the time, for example, on the basis of the time having been initially set and the number of vibrations of a crystal oscillator.

The driver 109 drives an output device that expresses the time of the sensor device 100 by light, sound, or the like, a lamp, for example, such as LED (Light Emitted Diode), a display, such as LCD (Liquid Crystal Display), a speaker, or the like. For example, when the clock 107 has reached a predetermined time, the driver 109 drives the output device with a pattern showing the time. The driver 109, for example, makes the lamp turn on with a predetermined color or a predetermined pattern, makes the display indicate a character or a code showing the time, or makes the speaker rumble with a predetermined oscillation frequency or a predetermined oscillation pattern.

(Information Processing Device)

The information processing device 200 includes an imaging section 201, a memory section 203, a clock 205, an analyzing section 207, a communication section 211, an image information acquiring section 212, an interval extracting section 213, a synchronization processing section 214, a time adapting section 216, a display processing section 218, and a display section 220. The analyzing section 207 includes a motion information acquiring section 208, a reference timing extracting section 209, and a trajectory analyzing section 210. In this connection, these constitutional components may include hardware (circuit) or a central processing unit, such as CPU, and a program for making this component function.

The imaging section 201 includes an image sensor for capturing an image, a lens, and a driving circuit for them. The image sensor includes a CMOS sensor, a CCD sensor, or the like. The imaging section 201 captures an image of the user who is wearing the sensor device 100 or a tool attached with the sensor device 100 and is playing a sport. This image is the above-mentioned play image. Therefore, in the play image, the sensor device 100 which a user is wearing directly or indirectly, may be reflected together with the user who is a photographic subject.

The memory section 203 stores temporarily or sustainably the data of the play image captured by the imaging section 201. At this time, the data of the play image are stored with a time stamp given by the clock 205. When sensor information has been received from the sensor device 100 through the communication section 211, the data of the play image may be provided to the analyzing section 207. Moreover, the play image having reflected a result of analysis in the analyzing section 207 or the play image to which additional information, such as a chapter image, has been set, may be stored again in the memory section 203.

The clock 205 regulates the time used in the information processing device 200. The clock 205 regulates the time, for example, on the basis of the time having been initially set and the number of vibrations of a crystal oscillator.

The analyzing section 207 analyzes the sensor information received from the sensor device 100 through the communication section 211. The motion information acquiring section 208 acquires information, such as acceleration, angular acceleration, and so on, as a plurality of pieces of motion information showing a series of motions of the same kind performed by a plurality of users, from the sensor device 100. The reference timing extracting section 209 extracts a reference timing on the basis of motion information, such as acceleration, angular acceleration, and so on. The trajectory analyzing section 210 analyzes the trajectory of the sensor device 200, the trajectory of a head portion, etc., on the basis of motion information, such as acceleration, angular acceleration, and so on.

The image information acquiring section 212 acquires a plurality of series of image information corresponding to motion information from the imaging section 201. As one example, this image information may be moving image information, or may be a series of image information including a plurality of still images. The interval extracting section 213 performs processing for drawing out a predetermined temporal range from a play image by making a reference timing correspond to a play image. The synchronization processing section 214 performs processing for synchronizing the image information corresponding to a series of motions of the same kind performed by a plurality of users on the basis of a reference timing. In the image information corresponding to a series of motions of the same kind performed by a plurality of users, the time adapting section 216 performs processing for adapting the time between reference timings. The display processing section 218 performs processing for displaying a plurality of pieces of image information.

The display section 220 includes a liquid crystal displays (LCD) or the like, and displays a plurality of pieces of image information in accordance with the processing of the display processing section 218.

The information processing device 200 acquires the motion information corresponding to a play image from a plurality of the sensor devices 100. In the below, description is given by citing, as an example, a case where the information processing device 200 acquires the data of a play image from the two sensor devices 100.

Figure 3:
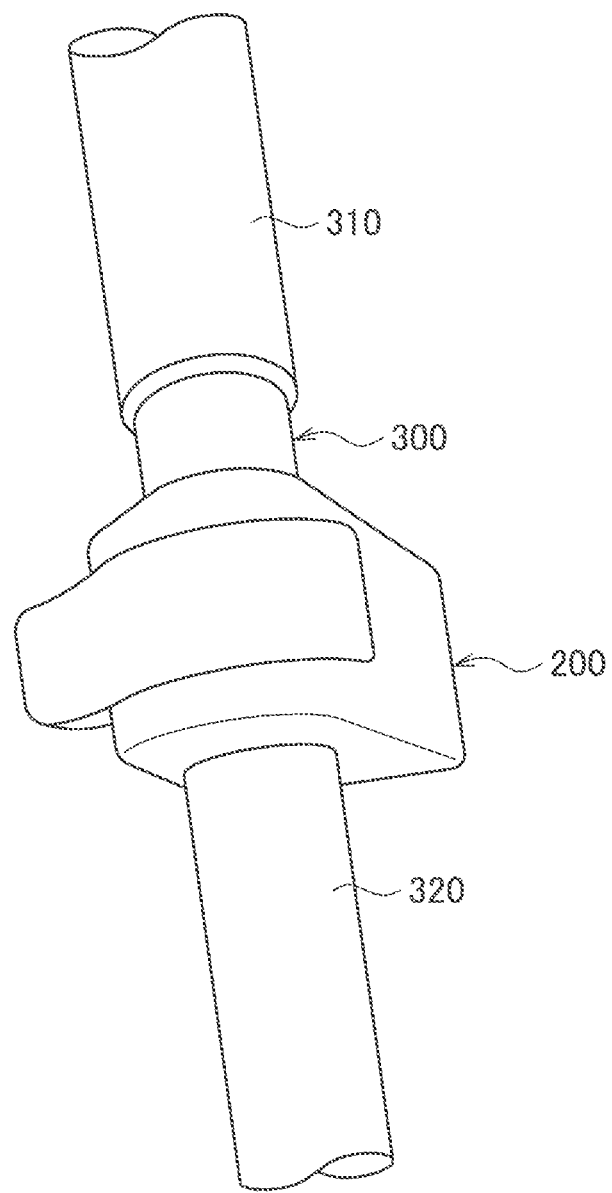
FIG. 3 is a schematic illustration showing a state where the present sensor device is attached to a shaft in the immediately below of a grip of a golf club.

In the below, description is given by citing, as an example, a case where a user performs a swing in golf. As shown in FIG. 3, as one example, the sensor device 100 is attached to a shaft 320 in the immediately below of a grip 310 of a golf club 300. In this case, on the basis of the trajectory of the sensor device 100, the trajectory of a head portion (club head) can be acquired by the geometric relationship between the position of the sensor device 100 and the position of the head portion.

In the present embodiment, in order to compare swings between two users, the two sensor devices 100 are attached to the two users, respectively. The information processing device 200 performs processing for extracting only a required portion from the data of a play image. For example, in the case of citing a case of golf, those useful as the data of a play image become three temporal ranges of (1) back-swing from the address to the top, (2) down-swing from the top to the impact, and (3) follow-swing from the impact to the finish. The analyzing section 207 of the information processing device 200 performs processing for drawing out these three temporal ranges on the basis of the detection values of the sensor 101.

For this reason, on the basis of the detection values of the sensor 101 of the sensor device 100, the analyzing section 207 analyzes the time of the address, the time of the impact, the time of the top, and the time of the finish. In concrete terms, the reference timing extracting section 209 extracts these times as reference timings. Then, the interval extracting section 213 performs processing for drawing out the above-described three temporal ranges (interval) by making these times correspond to the play image. By acquiring the data of play images from the plurality of the sensor devices 100 and by performing the similar processing, it becomes possible to display the swings in a state where the respective temporal ranges are adapted with respect to a plurality of players.

In this connection, before performing the processing for extracting the above-described three temporal ranges, in the sensor device 100 or the information processing device 200, it is possible to cut out beforehand play images for a predetermined time before and after the impact time that serves as a reference. With this, the processing loads of the sensor device 100 and the information processing device 200 are reduced, and in addition, it is possible to reduce the amount of memories to be used.

3. Processing Performed by Information Processing Device

Figure 4:
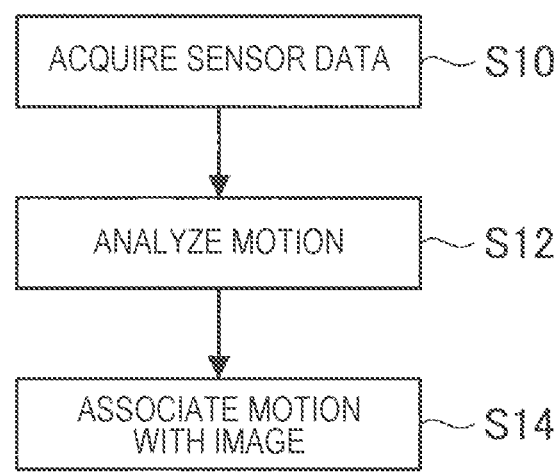
FIG. 4 is a flow chart showing processing performed by an analyzing section.

FIG. 4 is a flow chart showing the processing performed by the information processing device 200. First, in Step S10, the motion information acquiring section 208 acquires the data detected by the sensor 101 of the sensor device 100. In the next Step S12, on the basis of the detection values acquired in Step S10, the motion of the golf club is analyzed.

Figure 5:
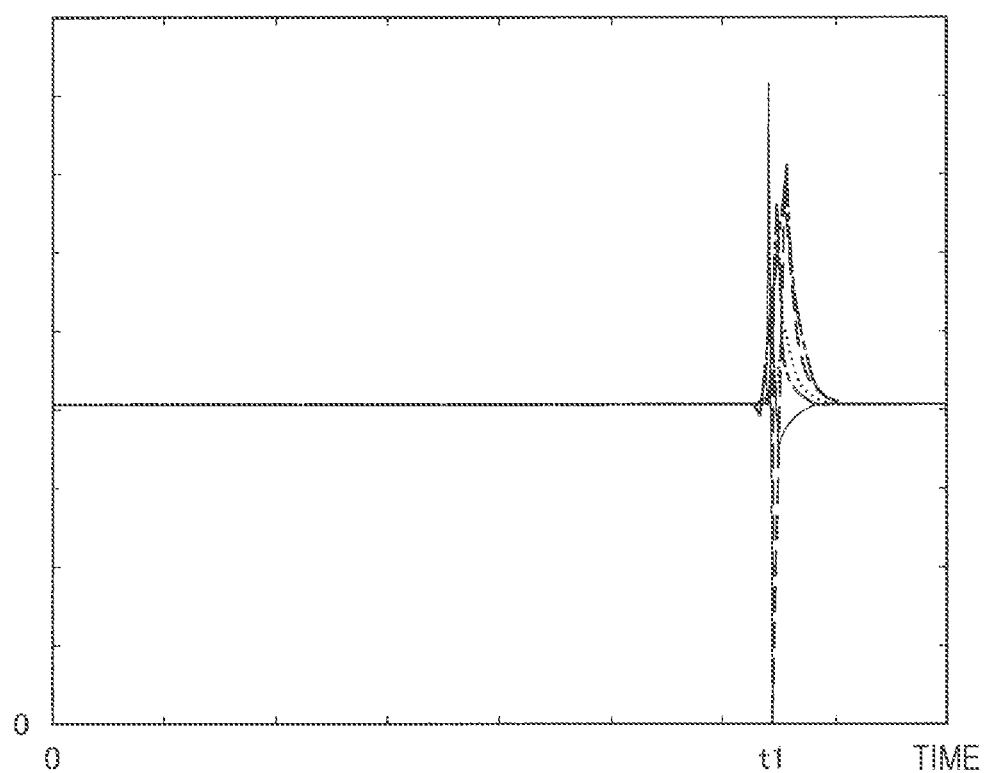
FIG. 5 is a graph showing one example of a measurement result of an acceleration sensor.

FIG. 5 is a graph showing one example of the measurement result of the acceleration sensor. There may be a case where the motion of the user during playing is accompanied by impact. In the case where the sensor device 100 is attached to the shaft 320 of the golf club 300 and a motion to hit a ball with the golf club 300 is performed, when the golf club 300 has hit a ball, impact is generated. The above impact appears as a steep change of acceleration as compared with the middle of the swing. In the case of describing with reference to FIG. 5, since the measured value of the acceleration sensor 200 is changing steeply in a short time in the vicinity of time t1 in FIG. 5, it may be considered that the impact has been generated in the vicinity of time t1. Therefore, the analyzing section 207 can determine the time t1 as a timing of impact on the basis of the result of having analyzed the acceleration.

Figure 6:
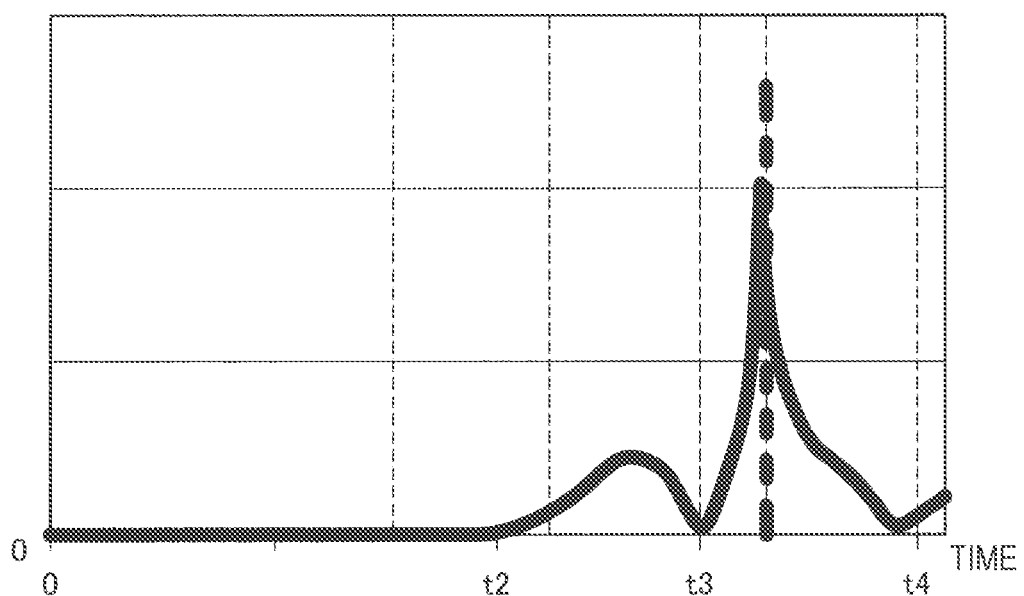
FIG. 6 is a characteristics diagram showing a trajectory A1 of a sensor section and a trajectory A2 of a head portion that have been obtained by analyzing the acceleration in the case where a sensor device is attached to the vicinity of a grip of a golf club.
Figure 7:
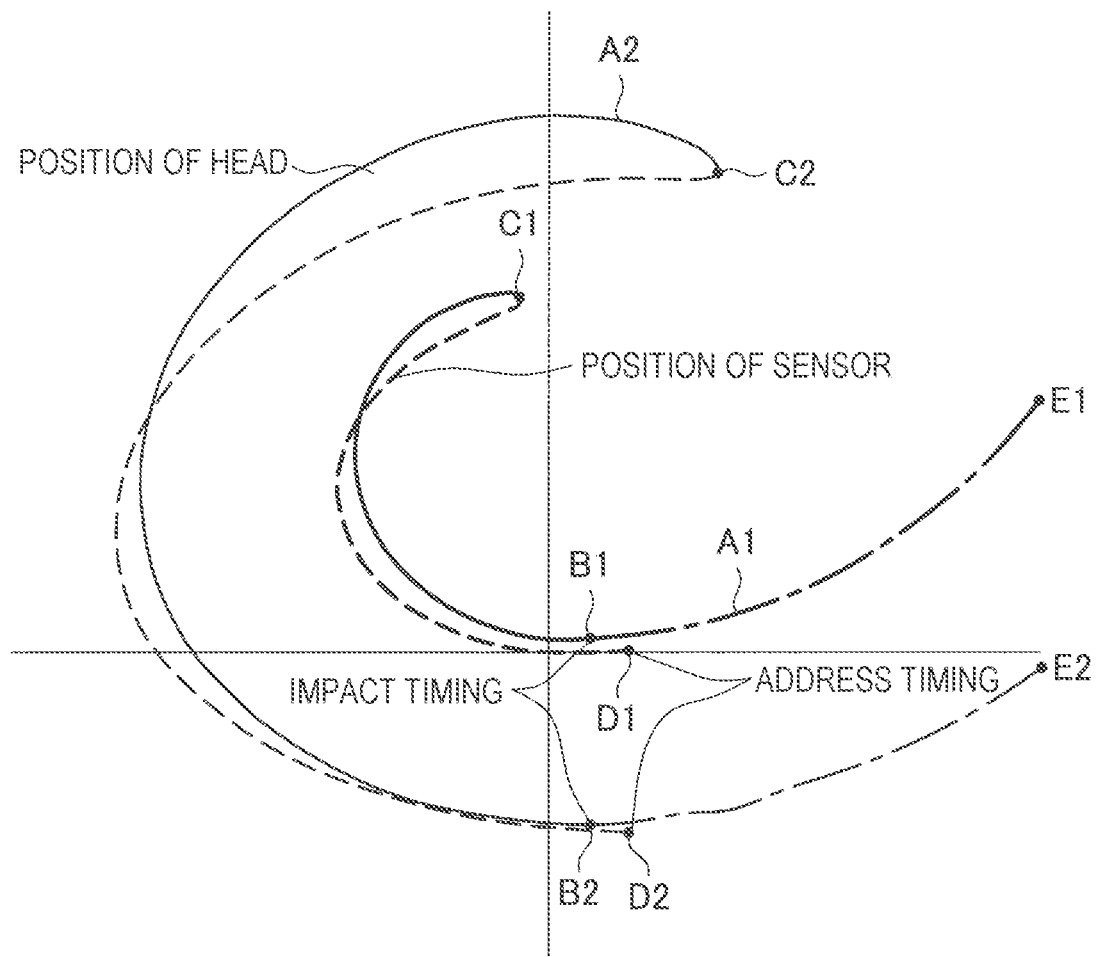
FIG. 7 is a characteristics diagram showing an angle of a sensor device obtained from an angular acceleration.

Moreover, the motion of the head portion can be analyzed by analyzing acceleration and angular acceleration, and is analyzed by the trajectory analyzing section 210. FIG. 6 is a characteristics diagram showing the angle (rotational position) of the sensor device 200 obtained from the angular acceleration. In concrete terms, a speed is calculated by integrating the acceleration, and further, by integrating the speed, the positional change of the head portion can be obtained. Similarly, by integrating the angular acceleration, the angle of the head portion can be obtained. FIG. 7 is a characteristics diagram showing the trajectory A1 of the sensor device 100 and the trajectory A2 of the head portion that have been analyzed on the basis of the acceleration and the angular acceleration in the case where the sensor device 100 has been attached to the vicinity of the grip of the club head. In this connection, on the basis of the trajectory A1 of the sensor device 100, it is possible to obtain the trajectory A2 of the head portion by the geometric relationship between the position of the sensor device 100 and the position of the head portion.

Since the detection values of the sensor 101 include time data, the analyzing section 207 can acquire the time information corresponding to arbitrary points on the trajectories A1 and A2. The reference timing extracting section 209 of the analyzing section 207 extracts the time t1 of the above-mentioned impact as a reference timing. Therefore, it is possible to obtain the positions B1 and B2 of the impact corresponding to the above-mentioned time t1 of the impact. Here, the position B1 is the position of the sensor 101 at the time of the impact, and the position B2 is the position of the head portion at the time of the impact.

Moreover, the analyzing section 207 can acquire the inflection points C1 and C2 on the trajectories A1 and A2 on the basis of the detection values of the acceleration and the angular acceleration. Here, the inflection point C1 corresponds to the position of the sensor 101 at the position of the top of the golf swing. Moreover, the inflection point C2 corresponds to the position of the head portion at the position of the top. In FIG. 7, at the time t2 and the time t3, since the amount of a change of the angle has become 0 (zero), it turns out that the rotation of the sensor device 200 has stopped temporarily. In the case of viewing the swing time serially, first, the motion of the club stops at the position of the address, and thereafter, the motion of the club stops at the position of the top. Therefore, the time t2 and the time t3 correspond to the respective positions of the address and the top. The reference timing extracting section 209 of the analyzing section 207 extracts the time corresponding to each of the respective positions of the address and the top as a reference timing. Thus, in the case where the time corresponding to each of the respective positions of the address and the top is known, it is possible to discriminate the positions D1 and D2 of the address and the positions C1 and C2 of the top on the trajectories A1 and A2. Here, the position D1 corresponds to the position of the sensor 101 at the position of the address, and the position D2 corresponds to the position of the head portion at the position of the address.

Therefore, on the basis of the time information corresponding to an arbitrary point on the trajectory A1, the position D1 of the address, the position C1 of the top, and the position B1 of the impact, the interval extracting section 213 can extract an interval (broken line) of the back-swing from the address to the top and an interval (solid line) of the down-swing from the top to the impact from the trajectory A1 of the sensor 101. Similarly, on the basis of the time information corresponding to an arbitrary point on the trajectory A2, the position D2 of the address, the position C2 of the top, and the position B2 of the impact, it is possible to extract an interval (broken line) of the back-swing from the address to the top and an interval (solid line) of the down-swing from the top to the impact from the trajectory A2 of the head portion.

Moreover, on the basis of the detection values of the acceleration and the angular acceleration, the analyzing section 207 can acquire the positions E1 and E2 of the finish on the trajectories A1 and A2. In FIG. 7, at the time t4, the amount of a change of the angle has become 0 (zero), and the rotation of the sensor device 200 has stopped temporarily. The positions E1 and E2 of the finish are at the time later than the positions B1 and B2 of the impact, and can be made a position where the sensor 101 and the head portion are standing still for a fixed period of time. The reference timing extracting section 209 of the analyzing section 207 extracts the time corresponding to the position of the finish as a reference timing. The position E1 corresponds to the position of the sensor 101 at the position of the finish, and the position E2 corresponds to the position of the head portion at the position of the finish. Therefore, on the basis of the time information corresponding to an arbitrary point on each of the trajectories A1 and A2, the positions B1 and B2 of the impact, and the positions E1 and E of the finish, the interval extracting section 213 can extract an interval (one-dot chain line) of the follow-swing from impact to the finish from each of the trajectories A1 and A2.

By doing as mentioned in the above, in Step S12 in FIG. 4, on the basis of the detection values of the sensor 101, the analysis of the motion of the golf club is performed.

Figure 8:
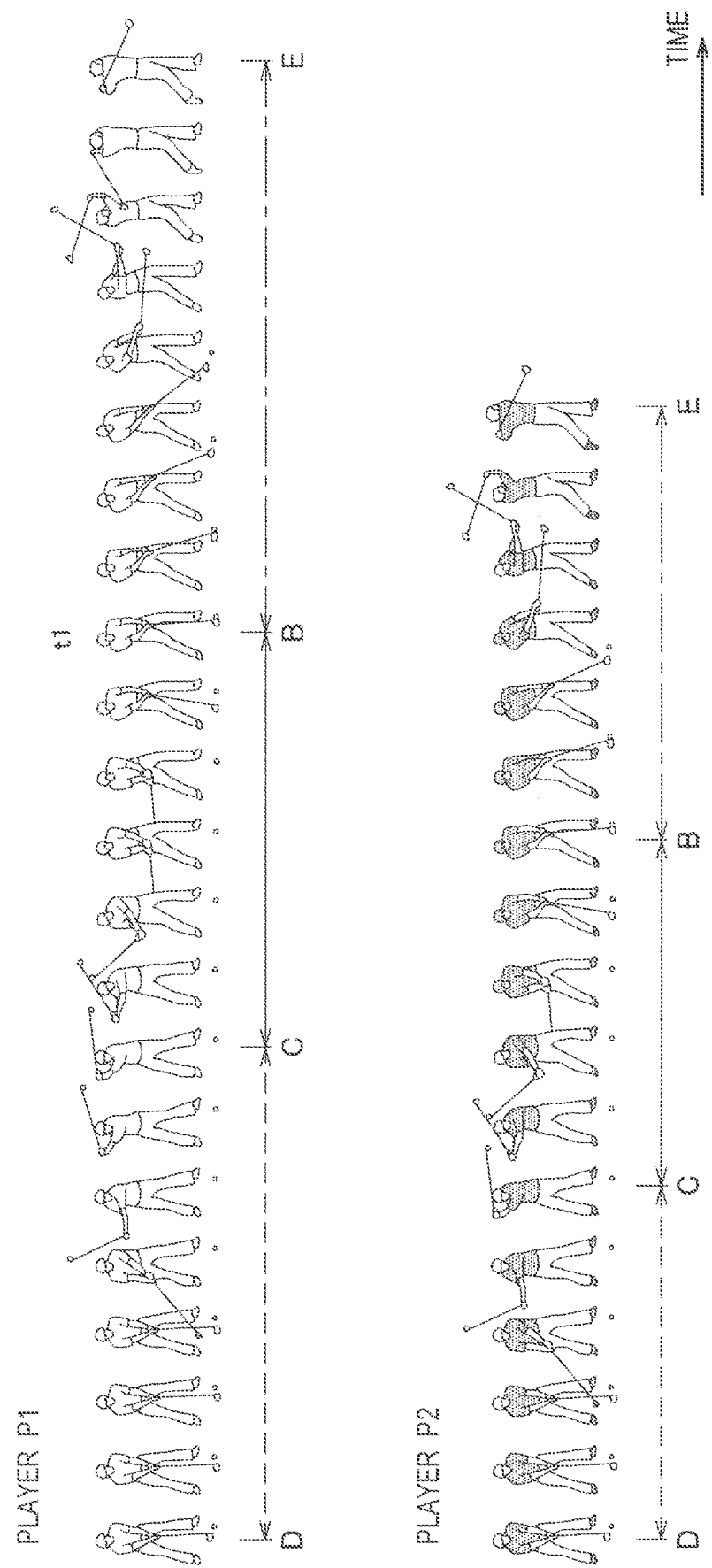
FIG. 8 shows an example of having extracted intervals from address to finish from a play image of a swing of each of two players P1 and P2 on the basis of the result of Step S12 in FIG. 4.

In the next Step S14, processing is performed for displaying the motion of the golf club analyzed in Step S12 and the play image by making them in association with each other. FIG. 8 shows an example of having extracted the temporal range from the address to the finish from the play image of the swing of each of the two players P1 and P2 on the basis of the result of Step S12. In FIG. 8, the motion of each of the players P1 and P2 is shown on the same time axis. Also in FIG. 8, the interval of the back-swing is shown with a broken line, the interval of the down-swing is shown with a solid line, and the interval of the follow-swing is shown with a one-dot chain line. Moreover, the position of the top is indicated with 'C', the position of the address is indicated with 'D', the position of the impact is indicated with 'B', and the position of the finish is indicated with 'E'.

As shown in FIG. 8, the time required for each of the back-swing, the down-swing, and the follow-swing is different for each player. In the example shown in FIG. 8, the time required for the player P1 from the address to the finish is longer than that for the player P2. For this reason, in the case of reproducing the moving image by arranging the swings of the both players from the address to the finish alongside, the moving image of the player P2 has ended ahead, and thereafter, the moving image of the player P1 ends. Accordingly, it becomes difficult to compare the swings of the both players while reproducing the moving image.

Figure 9:
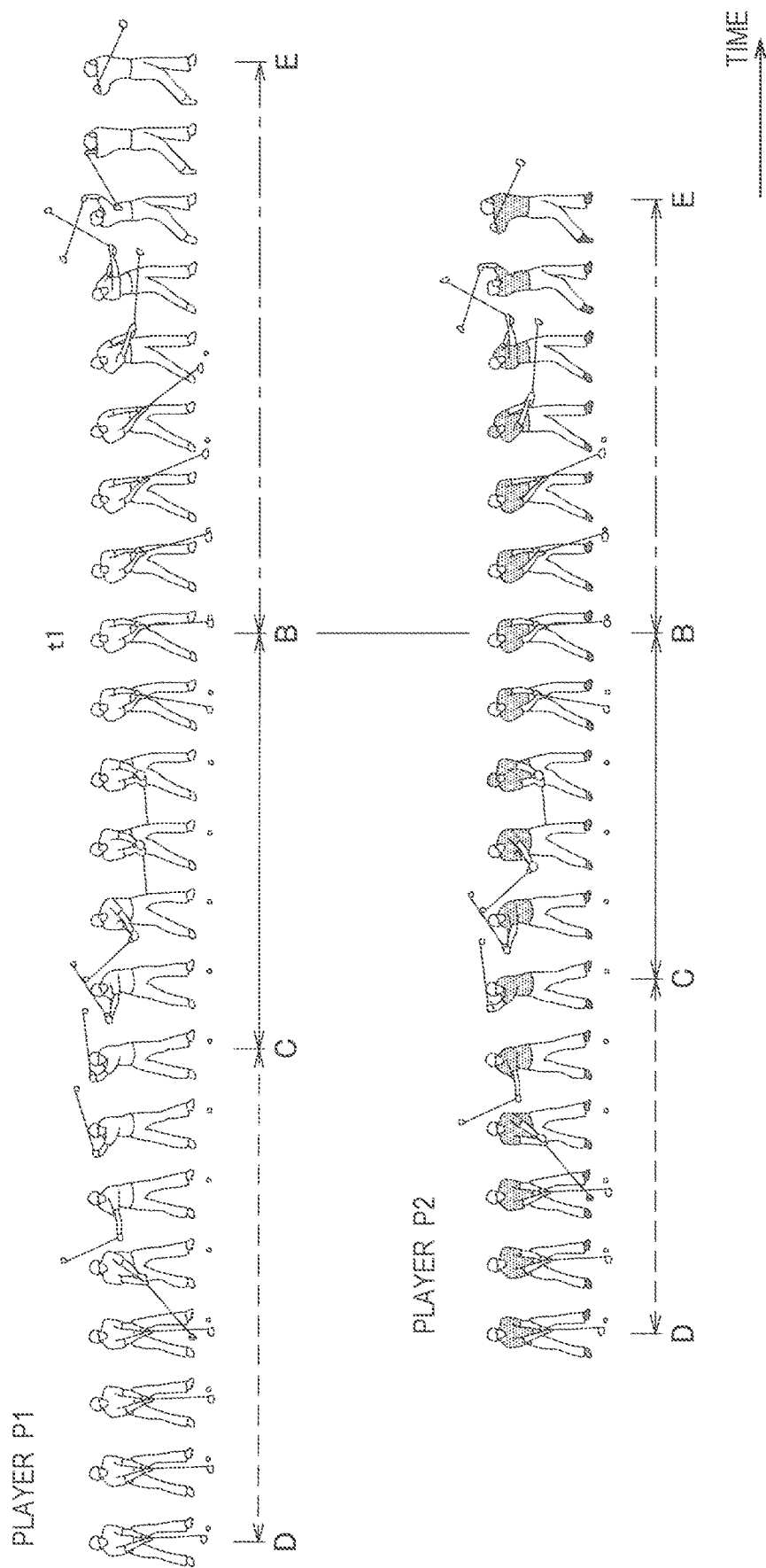
FIG. 9 is a schematic diagram showing a state where both play images have been synchronized at the time t1 of the impact as a reference, relative to FIG. 8.

For this reason, the synchronization processing section 214 performs processing for synchronizing the swings of the both players at the reference point during the swings of the player P1 and the player P2. As the reference point, the time t1 of the impact of the player P1 is used. Relative to FIG. 8, FIG. 9 shows a state where the both play images have been synchronized at the time t1 of the impact of the player P1 as a reference. In the state shown in FIG. 9, in the case of reproducing the moving images of the player P1 and the player P2, the reproducing of the moving image of the player P1 has been started ahead, and subsequently, the moving image of the player P2 is reproduced. However, since the respective times of the impact in both the moving images are coincident with each other, the easiness in viewing at the time of simultaneous reproduction is improved remarkably as compared with FIG. 8. With this, it becomes possible for a user to compare the respective swings of the player P1 and the player P2 by making the moment of impact as a reference.

Furthermore, in the present embodiment, after having synchronized the respective play images of the both players at the position of the impact as shown in FIG. 9, performed is the processing for adapting the time from the start of the reproducing of the moving image (the position of the address) to the end (the position of the finish). In concrete terms, the time adapting section 216 adapts the interval from the address to the top, the time from the top to the impact, and the reproducing time of the play image of each of the both players from the impact to the finish.

Figure 10:
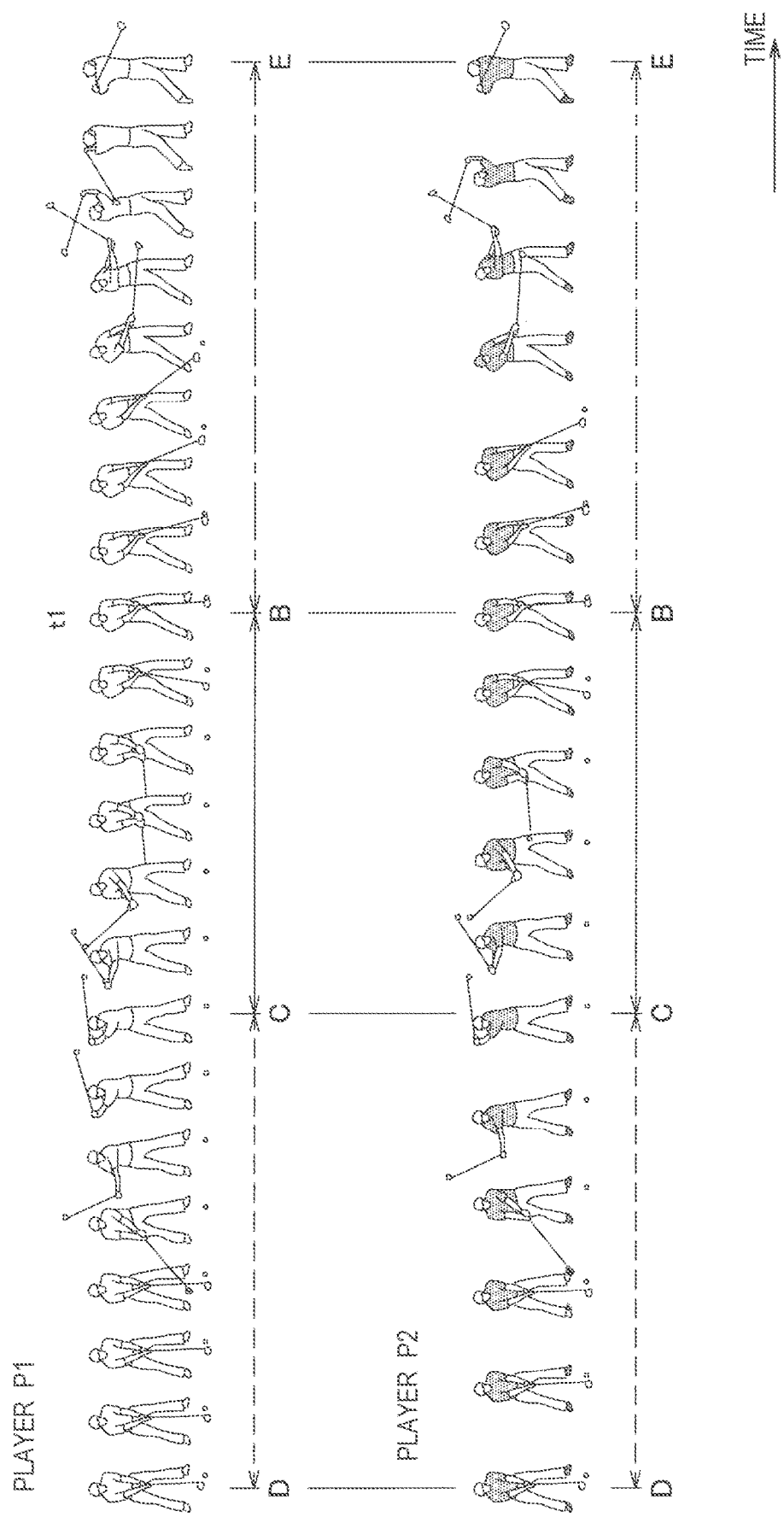
FIG. 10 is a schematic diagram showing a state where the respective reproducing times of the both play images are made coincident by prolonging the reproducing time of the play image of the player P2 by making the play image of the player P1 as a reference.

FIG. 10 shows a state where the respective reproducing times of the both play images are made coincident by prolonging the reproducing time of the play image of the player P2 by making the play image of the player P1 as a reference. At this time, on the basis of the analysis result by the sensor 101, a plurality of synchronous points are set up, and the reproducing speed is changed dynamically, whereby the synchronization is realized.

Figure 11:
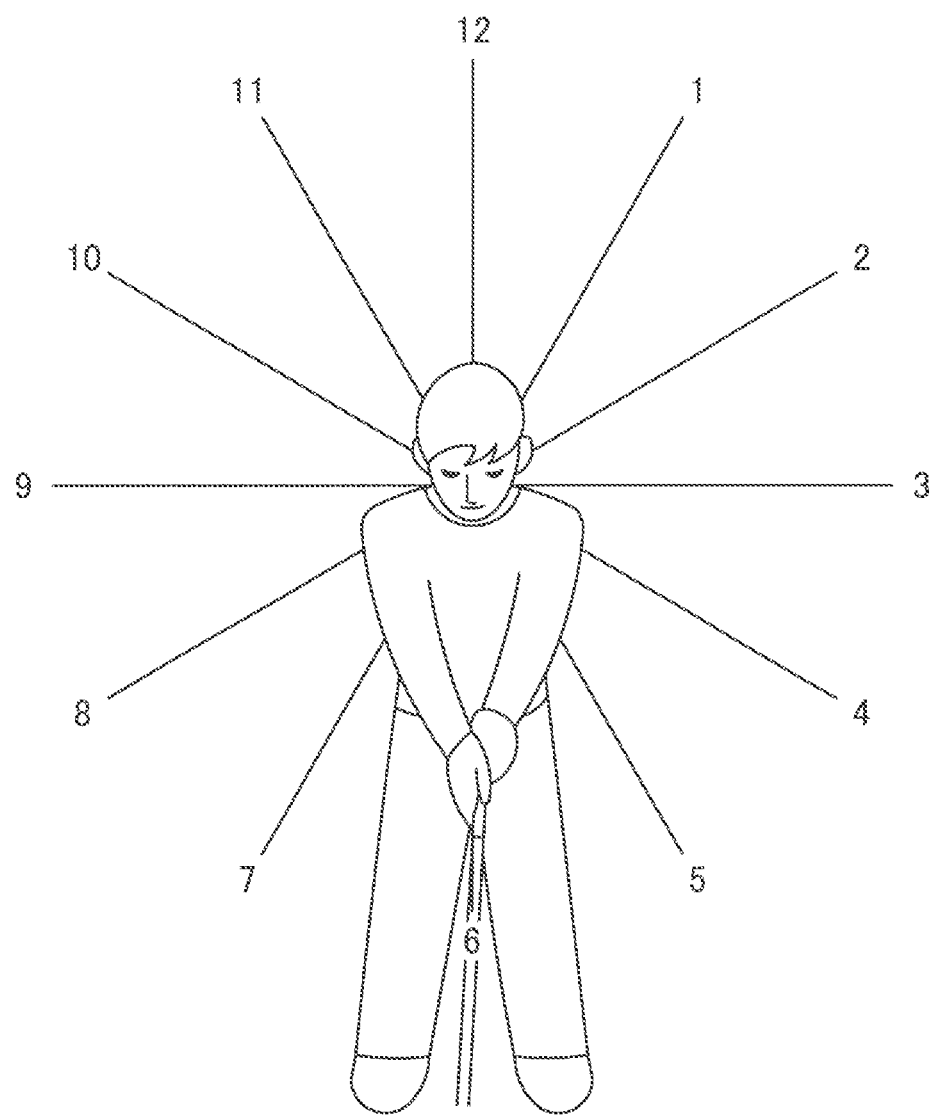
FIG. 11 is a schematic diagram showing a state where a golf swing is divided into a plurality of angles.

FIG. 11 shows a state where a golf swing is divided into a plurality of angles. In the case of the synchronization processing shown in FIG. 10, as one example, the reproducing speed is dynamically changed for each of the divided angles. As shown in FIG. 11, in the case where the position of the address is the position of '6' and the position of the top is the position of '11', an angle from the address to the top is equally divided by five, and the synchronization is performed for each of the divided angles. As mentioned in the above, the correlation between the arbitrary position and the time on the trajectories A1 and A2 is taken by the processing in Step S12. Accordingly, for example, in the play image of the player P1, at the time of the back-swing from the address toward the top, it is assumed that the time to reach the position of '7' advanced by one divided angle from the position of '6' of the address is T, the reproducing speed is changed so that, also in the play image of the player P2, the time to reach the position of '7' from the position of '6' of the address becomes T. Similarly, also with regard to the time to reach the position of '8' from the position of '7', the reproducing time of the play image of the player P2 is adapted so as to be coincident with the reproducing time of the play image of the player P1. By performing such processing for each of a range from the address to the top, a range from the top to the impact, and a range from the impact to the finish, it is possible to make the respective reproducing times of the play images of the player 1 and the player 2 coincide with each other without any discomfort. In this connection, by making a divided angle smaller, in the case of making the respective reproducing times coincide with each other, it is possible to display the moving images more smoothly. Moreover, in the case of changing the reproducing time at the time of switching the angles, by changing the reproducing time smoothly within a predetermined time including the switching timing, it is possible to display the moving images more smoothly.

With this, since the respective reproducing times of the play images of the player 1 and the player 2 are coincident with each, by reproducing the play images of the both players by arranging them alongside on the information processing device 200 side, it becomes possible to recognize a difference in swing certainly. Therefore, for example, by reproducing a professional golfer's image as the play image of the player 1, and by reproducing a user's own recorded image as the play image of the player 2, it also becomes possible to determine points etc. to be improved in the user's own swing relative to the professional golfer's swing from the images. Moreover, for example, by reproducing simultaneously the previous swing and the present swing of a user, it also becomes possible to confirm the degree of progress. In this connection, in the above-mentioned example, although the reproducing time of the player 2 has been adapted by making the reproducing time of the player 1 as a reference, the reproducing time of the player 1 may be adapted by making the reproducing time of the player 2 as a reference. Moreover, in the above-mentioned example, although the reproducing times have been adapted by synchronizing the moving images of two players, the reproducing times may be adapted by synchronizing the moving images of three or more players.

4. Example of Having Combined Motion Recognition and Image Processing

Figure 12:
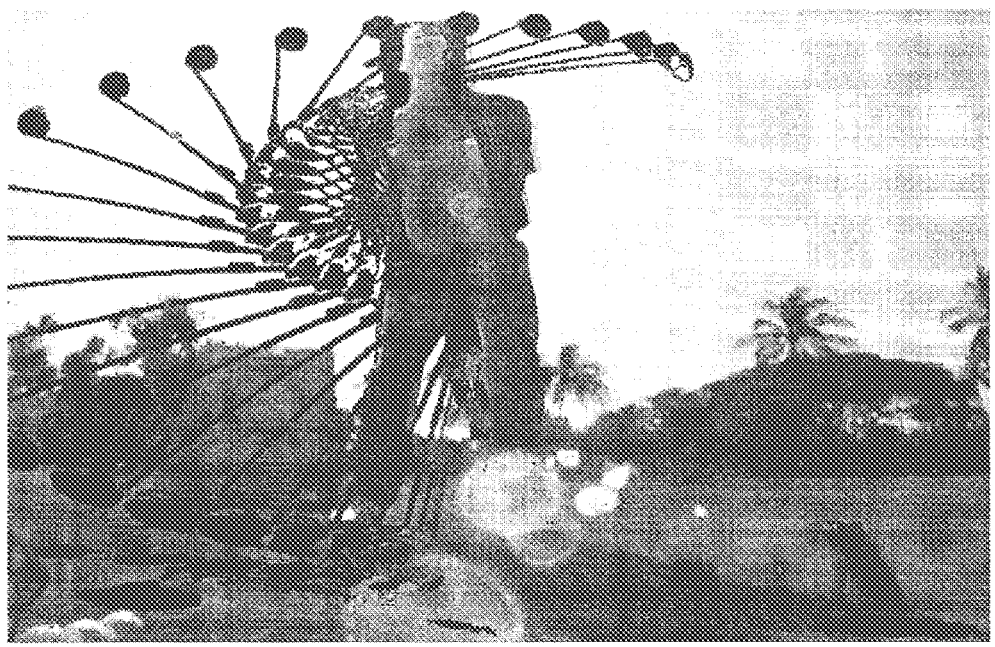
FIG. 12 is a schematic diagram showing an example in which a golf swing photographed by the information processing device 200 is shown by superimposing still images for each predetermined time.
Figure 13:
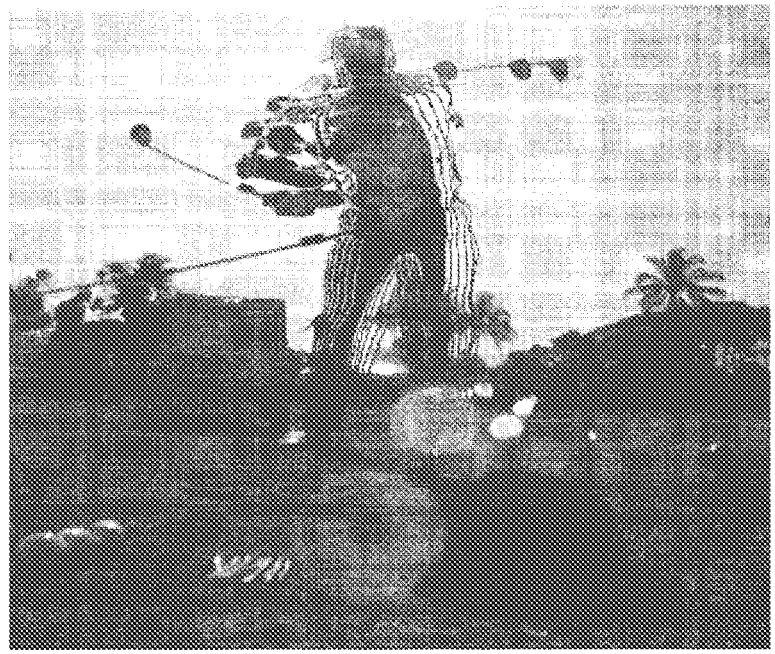
FIG. 13 is a schematic diagram showing an example in which a golf swing photographed by the information processing device 200 is shown by superimposing still images for each predetermined time.
Figure 14:
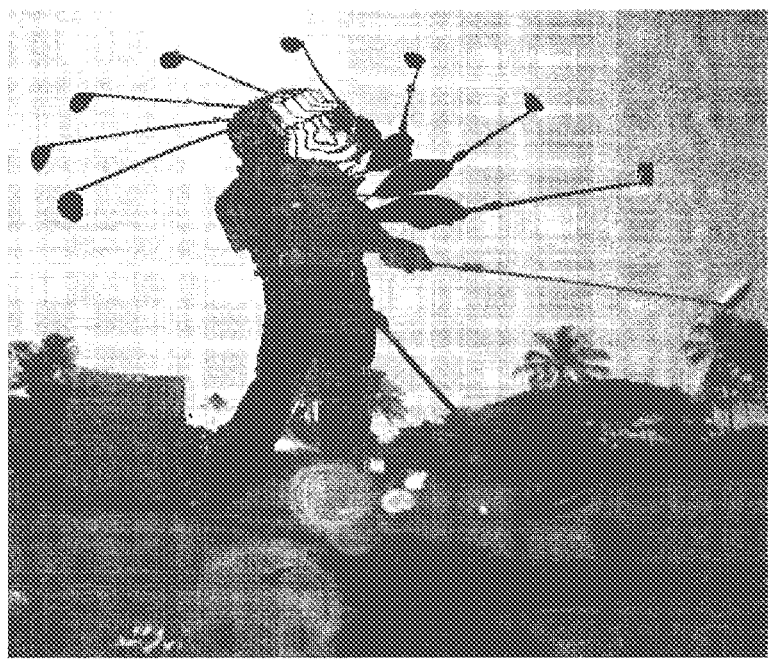
FIG. 14 is a schematic diagram showing an example in which a golf swing photographed by the information processing device 200 is shown by superimposing still images for each predetermined time.

Next, an example of having combined motion recognition and image processing by the sensor device 100 is described. FIG. 12 through FIG. 14 each is a schematic illustration showing an example in which a golf swing photographed by the information processing device 200 is shown by superimposing still images for each predetermined time. Here, FIG. 12 shows the back-swing, FIG. 13 shows the down-swing, and FIG. 14 shows the follow-swing. In the present embodiment, as mentioned in the above, it is possible to acquire the time information with regard to each of the position of the address, the position of the top, the position of the impact, and the position of the finish. For this reason, at the time of displaying a play image, each of the swings can be indicated with a different color so that the back-swing, the down-swing, and the follow-swing can be distinguished from each other. As one example, the back-swing shown in FIG. 12 is indicated in red, the down-swing shown in FIG. 13 is indicated in green, and the follow-swing shown in FIG. 14 is indicated in blue. The respective swings in FIG. 12 through FIG. 14 can be superimposed and displayed as one sheet of images. At this time, the display processing section 218 performs processing for displaying a plurality of consecutive still images, and displays the still images such that the respective display states of the still images become different for each temporal range determined in accordance with the time information (reference timing) of each of the position of the address, the position of the top, the position of the impact, and the position of the finish.

With this, a user who has visually recognized FIG. 12 through FIG. 14 can discriminate what kind of swing each of the back-swing, the down-swing, and the follow-swing has become, only by looking at a screen. In particular, by superimposing and displaying the back-swing, the down-swing, and the follow-swing, for example, it also becomes possible to recognize visually a difference in trajectory between the back-swing and the down-swing. Moreover, in the case of having reproduced the moving image of the swing, the reproducing has been completed for a short time. Accordingly, there may be also a possibility that there may exist a portion which cannot be recognized by an eye. As shown in FIG. 12 through FIG. 14, by superimposing and displaying the still image for each predetermined time, it becomes possible to recognize a fine motion certainly.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device, including:

a motion information acquiring section that acquires a plurality of pieces of motion information showing a series of motions of a same kind;

a reference timing extracting section that extracts a reference timing on the basis of a plurality of pieces of the motion information;

an image information acquiring section that acquires a plurality of series of image information corresponding to a plurality of pieces of the motion information; and a synchronization processing section that synchronizes a plurality of pieces of the image information on the basis of the reference timing.

(2)

The information processing device according to (1), in which the reference timing extracting section extracts a plurality of the reference timings corresponding to respective features of motions from a plurality of pieces of the motion information, and the information processing device includes a time adapting section that adapts a time between the reference timings in a plurality of pieces of the image information.

(3)

The information processing device according to (1) or (2), in which the motion information is acceleration or angular acceleration with regard to the motion.

(4)

The information processing device according to any of (1) to (3), including a sensor that detects the motion information.

(5)

The information processing device according to any of (1) to (4), in which the reference timing is a timing at which a change is added to the series of motions.

(6)

The information processing device according to (5), in which the reference timing is a timing at which impact is generated by hitting in the series of motions.

(7)

The information processing device according to (5), in which the reference timing is a timing at which the motion is stopped in the series of motions.

(8)

The information processing device according to (5), in which the reference timing is a start timing or an end timing of the series of motions.

(9)

The information processing device according to any of (1) to (8), including a display processing section that performs processing for displaying a plurality of pieces of the image information.

(10)

The information processing device according to (9), in which the display processing section performs processing for displaying a plurality of consecutive still images on the basis of the image information.

(11)

The information processing device according to (10), in which the display processing section displays the still images such that display states of the still images become different for each temporal range determined by the reference timing.

(12)

The information processing device according to any of (1) to (11), in which a plurality of pieces of the motion information correspond to a series of the motions of a same kind performed by a plurality of users.

(13)

The information processing device according to any of (1) to (11), in which a plurality of pieces of the motion information correspond to a series of the motions of a same kind performed by a single user.

(14)

A sensor device, including:

a sensor that detects a plurality of pieces of motion information showing a series of motions of a same kind; and a transmitting section that transmits the motion information to an information processing device to make an information processing device perform processing for extracting a reference timing on the basis of a plurality of pieces of the motion information, processing for acquiring a plurality of series of image information corresponding to a plurality of pieces of the motion information, and processing for synchronizing a plurality of pieces of the image information on the basis of the reference timing.

(15)

An information processing system, including:

a sensor device that detects a plurality of pieces of motion information showing a series of motions of a same kind; and an information processing device that includes a motion information acquiring section that acquires the motion information from the sensor device, a reference timing extracting section that extracts a reference timing on the basis of a plurality of pieces of the motion information, an image information acquiring section that acquires a plurality of series of image information corresponding to a plurality of pieces of the motion information, and a synchronization processing section that synchronizes a plurality of pieces of the image information on the basis of the reference timing.

(16)

The information processing system according to (15), in which the reference timing extracting section extracts a plurality of the reference timings corresponding to respective features of motions from a plurality of pieces of the motion information, and the information processing device includes a time adapting section that adapts a time between the reference timings in a plurality of pieces of the image information.

REFERENCE SIGNS LIST 208 motion information acquiring section
209 reference timing extracting section
212 image information acquiring section
214 synchronization processing section
216 time adapting section
218 display processing section

The invention claimed is:

1. An information processing device, comprising:
   a motion information acquiring section configured to acquire a plurality of pieces of motion information indicating a series of motions of a same kind for each of a first user and a second user;
   a reference timing extracting section configured to extract a plurality of reference timings corresponding to respective features of motions from the plurality of pieces of motion information;
   an image information acquiring section configured to acquire a first plurality of series of image information associated with the first user and a second plurality of series of image information associated with the second user, wherein the first plurality of series of image information and the second plurality of series of image information correspond to the plurality of pieces of motion information;
   a synchronization processing section configured to synchronize the first plurality of series of image information and the second plurality of series of image information based on at least one reference timing of the plurality of reference timings; and
   a time adapting section configured to change a reproducing speed of the second plurality of series of image information between the plurality of reference timings with respect to the first plurality of series of image information, such that a reproducing time of the second plurality of series of image information is synchronized with a reproducing time of the first plurality of series of image information.

2. The information processing device according to claim 1, wherein the plurality of pieces of motion information comprises at least one of acceleration or angular acceleration with regard to the series of motions.

3. The information processing device according to claim 1, further comprising a sensor configured to detect the plurality of pieces of motion information.

4. The information processing device according to claim 1, wherein the at least one reference timing is a timing at which a change is added to the series of motions.

5. The information processing device according to claim 4, wherein the at least one reference timing is one of a start timing or an end timing of the series of motions.

6. The information processing device according to claim 1, wherein the at least one reference timing is a timing at which an impact is generated by a hitting action in the series of motions.

7. The information processing device according to claim 1, wherein the at least one reference timing is a timing at which motion is stopped in the series of motions.

8. The information processing device according to claim 1, further comprising a display processing section configured to
   control display of the first plurality of series of image information and the second plurality of series of image information.

9. The information processing device according to claim 8, wherein the display processing section is further configured to control display of a plurality of consecutive still images based on the first plurality of series of image information.

10. The information processing device according to claim 9, wherein the display processing section is further configured to control the display of the plurality of consecutive still images such that display states of the plurality of consecutive still images become different for each temporal range determined by the at least one reference timing.

11. The information processing device according to claim 1, wherein the plurality of pieces of motion information corresponds to the series of motions of a plurality of users.

12. The information processing device according to claim 1, wherein the plurality of pieces of motion information corresponds to the series of motions of a single user.

13. A sensor device, comprising:
a sensor configured to detect a plurality of pieces of motion information indicating a series of motions of a same kind; and
a transmitting section configured to transmit the plurality of pieces of motion information to an information processing device to cause the information processing device execute a plurality of processes to:
  extract a plurality of reference timings corresponding to respective features of motions from the plurality of pieces of motion information;
  acquire a first plurality of series of image information associated with a first user and a second plurality of series of image information associated with a second user, wherein the first plurality of series of image information and the second plurality of series of image information correspond to the plurality of pieces of motion information;
  synchronize the first plurality of series of image information and the second plurality of series of image information based on at least one reference timing of the plurality of reference timings; and
  change a reproducing speed of the second plurality of series of image information between the plurality of reference timings with respect to the first plurality of series of image information, such that a reproducing time of the second plurality of series of image information is synchronized with a reproducing time of the first plurality of series of image information.

14. An information processing system, comprising:
a sensor device configured to detect a plurality of pieces of motion information indicating a series of motions of a same kind; and
an information processing device that includes:
  a motion information acquiring section configured to acquire the plurality of pieces of motion information for each of a first user and a second user from the sensor device;
  a reference timing extracting section configured to extract a plurality of reference timings corresponding to respective features of motions from the plurality of pieces of motion information;
  an image information acquiring section configured to acquire a first plurality of series of image information associated with the first user and a second plurality of series of image information associated with the second user, wherein the first plurality of series of image information and the second plurality of series of image information correspond to the plurality of pieces of motion information;
  a synchronization processing section configured to synchronize the first plurality of series of image information and the second plurality of series of image information based on at least one reference timing of the plurality of reference timings; and
  a time adapting section configured to change a reproducing speed of the second plurality of series of image information between the plurality of reference timings with respect to the first plurality of series of image information, such that a reproducing time of the second plurality of series of image information is synchronized with a reproducing time of the first plurality of series of image information.

* * * * *